United States Patent [19]

Anderson

[11] Plant 4,093

[45] Aug. 23, 1977

[54] NECTARINE TREE

[75] Inventor: Frederic W. Anderson, Merced, Calif.

[73] Assignee: The Burchell Nursery, Inc., Modesto, Calif.

[21] Appl. No.: 728,622

[22] Filed: Oct. 1, 1976

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is large, vigorous, upright to spreading, medium in size and texture of the trunk and branches, foliated with large to medium size, medium thick, lanceolate, acutely pointed leaves having a crenate margin and globose glands, blooms mid-season with large flowers, and a regular and very productive bearer of large, symmetrical, globose, freestone fruit having yellow skin substantially overspread with red, and yellow flesh.

1 Drawing Figure

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The present variety of nectarine tree was originated by me, in my experimental nursery and orchard located as aforesaid, as an $F_1$ cross of the Red Diamond nectarine (U.S. Plant Pat. No. 3,165), the seed parent, and the Sun Grand nectarine (U.S. Plant Pat. No. 974), the pollen parent. The variety, as thus originated, and under careful and continuing observation, evidenced—upon bearing fruit—certain novel characteristics which were commercially desirable, and I, therefore, undertook asexual reproduction of the variety preparatory to introducing it to the trade.

ASEXUAL REPRODUCTION OF THE VARIETY

Subsequent to origination and selection by me of the present variety of nectarine tree, in the manner above described, I asexually reproduced it by top-working on mature trees in my said experimental orchard, and—in maturity—such reproductions ran true to the original tree in all respects.

SUMMARY OF THE VARIETY

The present variety of nectarine tree is large, vigorous, upright to spreading, medium in size and texture of the trunk and branches, foliated with large to medium size, medium thick, lanceolate, acutely pointed leaves having a crenate margin and globose glands, blooms mid-season with large flowers, and a regular and very productive bearer of large, symmetrical, globose, freestone fruit having yellow skin substantially overspread with red, and yellow flesh; the variety being particularly characterized by fruit embracing both the bright red exterior color and the firm flesh of the fruit of the Red Diamond nectarine, the seed parent, and the very firm flesh of the fruit of the Sun Grand nectarine, the pollen parent, but ripening about ten days earlier than said Sun Grand nectarine.

BRIEF DESCRIPTION OF THE DRAWING

The drawing is an illustration, by photographic reproduction in color, of leaves and fruit of the variety; one of the fruit being cut into halves to expose the flesh, with the stone remaining in one such half.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Size.*—Large.
- *Vigor.*—Vigorous.
- *Growth.*—Upright to spreading.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium.

Leaves:
- *Size.*—Large to medium; average length of blade — $5\frac{1}{4}''$; average width of blade — $1\frac{1}{4}''$.
- *Form.*—Lanceolate; acutely pointed.
- *Thickness.*—Medium.
- *Margin.*—Crenate.
- *Petiole.*—Medium length — average $\frac{1}{2}''$; medium thickness.
- *Glands.*—Number and position — usually 2–3 on petiole and 1–4 on blade; alternate; globose.
- *Color.*—Top Side — Medium green (23-J-8); under side — Lighter green (22-K-7).

Flowers:
- *Blooming period.*—Mid-season; medium, as compared with other varieties.
- *Size.*—Large.

Fruit:
- *Maturity when described.*—Eating ripe — July 12, 1976.
- *Date of first picking.*—July 2, 1976.
- *Date of last picking.*—July 12, 1976.
- *Size.*—Large; uniform; average diameter axially — $2\frac{3}{8}''$; average transversely in suture plane — $2\frac{1}{2}''$.
- *Form.*—Symmetrical; globose.

*Suture.*—Shallow; extends from base to apex, with slight depression beyond pistil point.
*Cavity.*—Rounded.
*Base.*—Rounded.
*Apex.*—Short.
*Pistil point.*—Apical.

Skin:
*Thickness.*—Medium.
*Texture.*—Medium.
*Tendency to crack.*—None noted.
*Down.*—Wanting.
*Color.*—Yellow (11-L-8) substantially overspread with red (5-L-6) shading to darker red (7-L-6).

Flesh:
*Amygdalin.*—Scant to wanting.
*Juice.*—Abundant; rich.
*Texture.*—Firm; crisp; meaty; melting.
*Ripens.*—Evenly.
*Flavor.*—Subacid; delicate.
*Aroma.*—Wanting.
*Eating Quality.*—Good.
*Color.*—Yellow (11-L-5) with slight flecking of red when full ripe.
*Surface of pit cavity.*—Yellow with red.

Stone:
*Type.*—Free.
*Size.*—Large to medium; average length — 1 3/16"; average breadth — 1 1/16"; average thickness — 9/16".
*Form.*—Oval.
*Sides.*—Equal.
*Tendency to split.*—Slight.

*Kernel.*—Sweet.
*Color.*—Brown (7-H-11).

Use: Market — local; dessert; canning.
Keeping quality: Good.
Resistance to insects and diseases: No unusual susceptibilities noted.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is large, vigorous, upright to spreading, medium in size and texture of the trunk and branches, foliated with large to medium size, medium thick, lanceolate, acutely pointed leaves having a crenate margin and globose glands, blooms mid-season with large flowers, and a regular and very productive bearer of large, symmetrical, globose, freestone fruit having yellow skin substantially overspread with red, and yellow flesh; the variety being particularly characterized by fruit embracing both the bright red exterior color and the firm flesh of the fruit of the Red Diamond nectarine, the seed parent, and the very firm flesh of the fruit of the Sun Grand nectarine, the pollen parent, but ripening about ten days earlier than said Sun Grand nectarine.

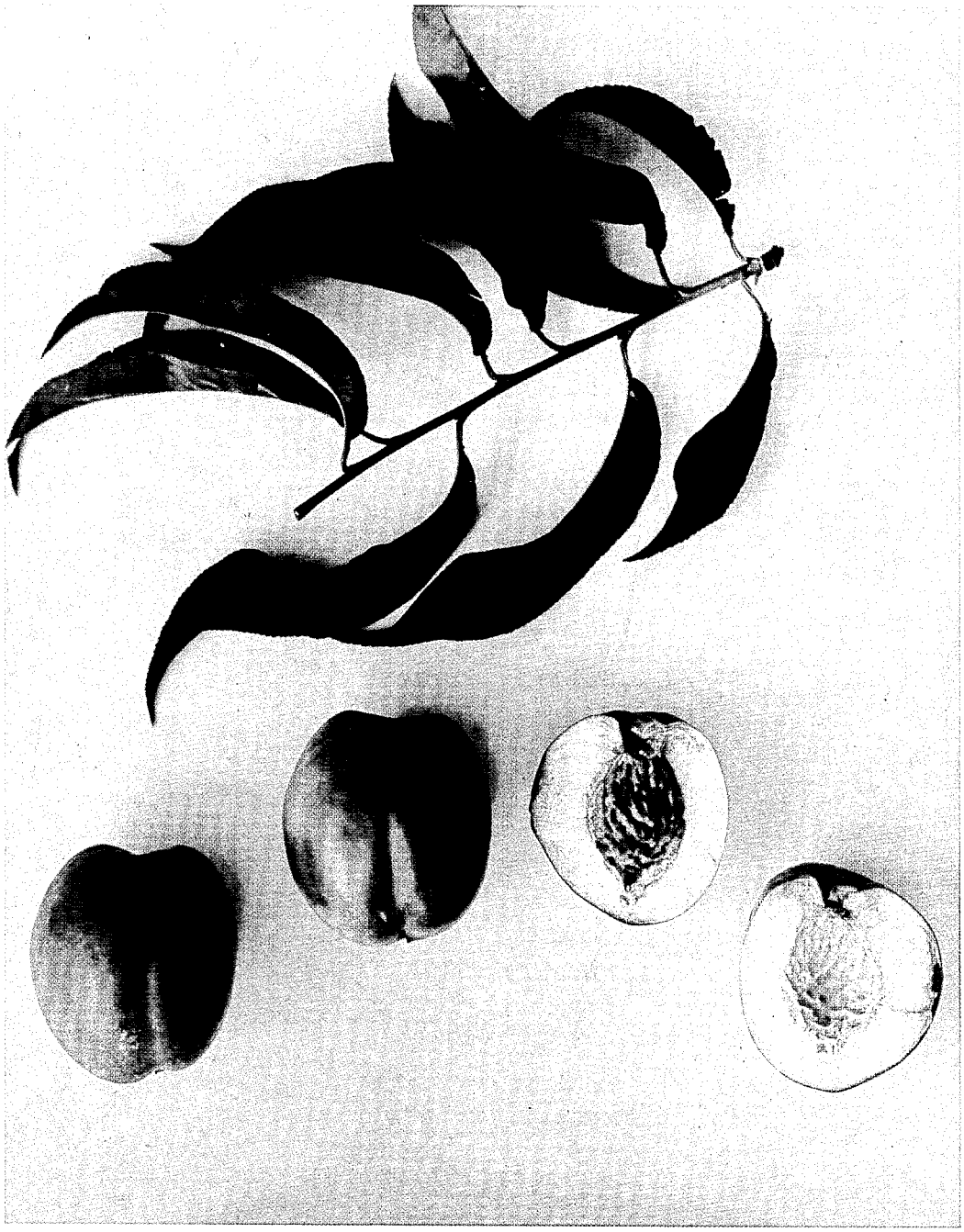

* * * * *